United States Patent [19]

Watson

[11] Patent Number: 5,324,251
[45] Date of Patent: Jun. 28, 1994

[54] DEVICE FOR FLEXING OR STRAIGHTENING A JOINT

[76] Inventor: Harold K. Watson, 3 Fairmont St., Wethersfield, Conn. 06109

[21] Appl. No.: 44,813

[22] Filed: Apr. 8, 1993

[51] Int. Cl.⁵ ............................. A61F 5/04; A61F 5/10
[52] U.S. Cl. ....................................... 602/16; 602/22; 602/30
[58] Field of Search ............... 602/20, 21, 22, 30, 602/16; 128/26; 482/47, 48

[56] References Cited

U.S. PATENT DOCUMENTS

| | | |
|---|---|---|
| 1,389,741 | 9/1921 | Cotton ........................... 602/21 |
| 2,357,323 | 9/1944 | Goldberg ........................ 602/21 |
| 3,769,970 | 11/1973 | Swanson . |
| 3,794,019 | 2/1974 | Ritland et al. . |
| 4,456,002 | 6/1984 | Barber et al. . |
| 4,862,877 | 9/1989 | Barber . |
| 4,949,711 | 8/1990 | Gyovai et al. . |
| 5,183,458 | 2/1993 | Marx ............................. 602/22 |

FOREIGN PATENT DOCUMENTS

| | | | |
|---|---|---|---|
| 242737 | 5/1946 | Switzerland ..................... 602/22 |
| 620952 | 2/1947 | United Kingdom ............... 602/21 |

*Primary Examiner*—Steven A. Bratlie
*Attorney, Agent, or Firm*—Chilton, Alix & Van Kirk

[57] ABSTRACT

A splint for flexing or straightening a joint of a hand or foot. The splint includes a support plate including a planar portion to be mounted on the hand or foot in a stationary position relative to one of the distal bone and proximal bone of the joint. A rod is mounted above the support plate and serves as a pivot axis for one or more elongated bent bars. A finely threaded, adjustable screw is mounted at one end of each bar and has a tip which bears against the support plate. A support pad is adjustably mounted at the other end of each bar and engages the hand or foot along the other of the proximal bone and distal bone of the joint. The pivotal angle of the bar relative to the support plate is vernierly adjusted by turning the adjustment screw. As a result of adjustment of this pivotal angle, the joint can be gradually flexed or straightened. The splint is particularly well-suited for flexing a metacarpophalangeal (MP) joint of hand.

21 Claims, 1 Drawing Sheet

DEVICE FOR FLEXING OR STRAIGHTENING A JOINT

BACKGROUND OF THE INVENTION

The present invention relates generally to splints, and more particularly relates to a device for flexing or straightening one or more joints of a hand or foot.

When the flexion of the metacarpophalangeal (MP) joints of a hand is limited as a result of injury or illness, it is known to use a spring-type flexion splint, such as the knuckle splint described in U.S. Pat. No. 4,456,002, in order to induce flexion of the joints. However, known devices of this type do not provide for individual control of the pressure exerted on each individual joint. Furthermore, the tension or force exerted by such devices on a joint cannot be readily adjusted in very small increments.

SUMMARY OF THE INVENTION

An object of the invention is to provide a flexion device for a hand or foot joint which applies an easily changeable, vernierly adjustable, and precisely controllable non-elastic force to the joint to set the joint in a flexed or straightened position at a rate which the doctor or patient can select.

Another object of the invention is to provide a flexion device which can be individually adjusted to induce different degrees of flexion upon different joints of a hand or foot.

Yet another object of the invention is to provide a joint flexing or straightening device which can be used on selected joints of a hand or foot.

A further object of the invention is to provide a comfortable joint flexing device for a hand which results in minimal interference with the use of the hand.

Another object of the invention is to provide a joint flexing or straightening device which can be adapted to fit the hand of the user, and can therefore be used for hands of varying sizes.

Another object of the invention is to provide a relatively inexpensive and simple-to-use joint flexing or straightening device which can be initially applied and adjusted by a physician, and is simple enough for the patient to use and adjust without further assistance from the physician.

Yet another object of the invention is to provide a knuckle splint which includes a flexion device of the type described above.

Other objects of the invention will be in part obvious and in part pointed out more in detail hereinafter.

The invention in a preferred form is a splint for flexing a metacarpophalangeal joint of a hand. The splint includes bar support means to be mounted on the hand in a stationary position relative to the metacarpals. One or more bars are pivotally connected to the bar support means. A finger support pad is formed on each bar at one end thereof and is adapted to engage the dorsal side of a finger along a proximal phalanx. An adjustment means is formed on the other end of each bar to allow for individual, vernier adjustment of the pivotal angle of the bar relative to the bar support means when the finger support pad engages a finger. During adjustment and pivoting, the bars remain substantially rigid.

The adjustment means preferably is a threaded adjustment screw which is threadably connected to the bar. The screw has a head which can be manually rotated by the physician or patient, and a tip which bears against the support means.

In a particularly preferred form of the invention, the bar support means includes a support plate which extends across the dorsal side of the hand, a transverse rod spaced from the support plate, which serves as a pivot axis for the bars, and means for holding the rod in a stationary position relative to the support plate. The rod serves as a pivot axis for the bars.

The one or more bars preferably are bent to generally follow the angle of the MP joint to be flexed. Furthermore, the splint can be configured such that the longitudinal position of the support pads along the bars can be adjusted to fit the hand of a particular patient.

Another preferred form of the invention is a splint for flexing or straightening a joint which connects a proximal bone and a distal bone of a hand or foot. The splint includes bar support means to be supported on a hand or foot in a generally stationary position relative to one of the proximal bone and the distal bone. The support means includes a support plate, a transverse rod spaced from the support plate, and means for holding the rod in a stationary position relative to the support plate. The rod serves as a pivot axis for a first bar which is pivotally connected to the rod. A support pad is formed at one end of the first bar for engaging the hand or foot along the other of the proximal bone and distal bone. The splint also includes adjustment means formed at the other end of the first bar, which preferably is an adjustment screw, for vernierly adjusting the pivotal angle of the first bar relative to the support plate when the support pad engages the hand or foot. Several bars of similar configuration can be slidably mounted along the rod and can be positioned such that the support pads formed thereon engage different fingers and/or toes.

The invention accordingly consists in the features of construction, combination of elements and arrangement of parts which will be exemplified in the construction hereafter set forth and the scope of the application which will be indicated in the appended claims.

DETAILED DESCRIPTION OF THE PREFERRED EMBODIMENT

Figure 1:
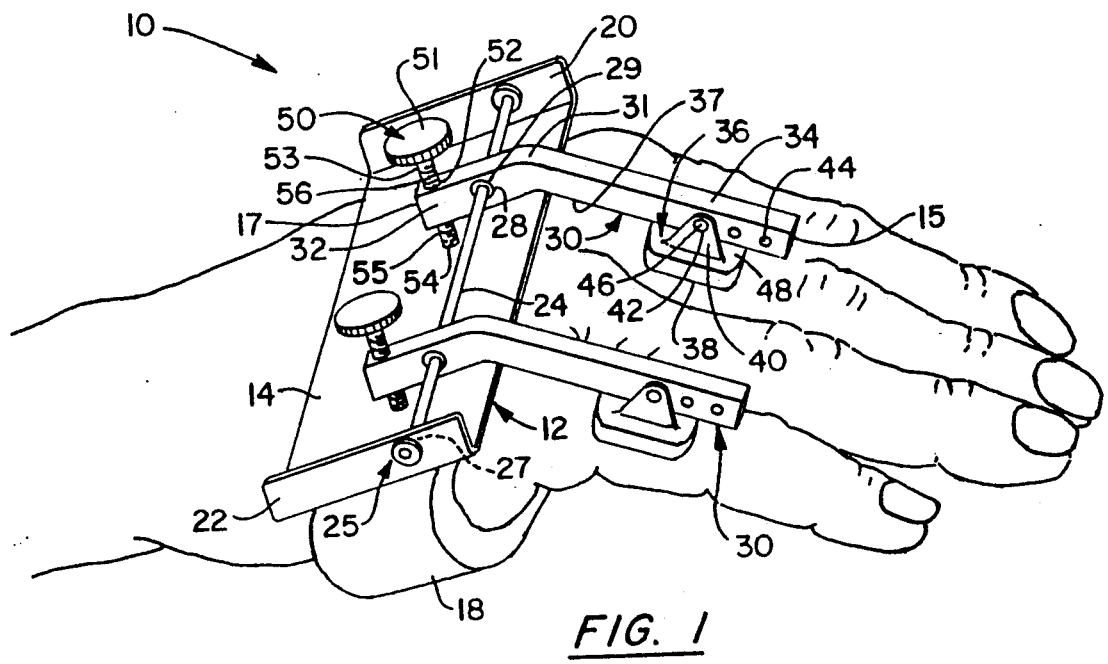
FIG. 1 shows a perspective view of the joint flexing device of the invention positioned for use on a hand.

Referring now to the drawing in greater detail wherein like reference numerals indicate like parts throughout the Figs., a joint flexion device 10 according to the present invention is shown in FIG. 1 as being applied to a hand. Briefly stated, the joint flexion device 10 includes a splint or bar support plate 12 having a generally flat, rectangular planar portion 14 which is mounted across the dorsal side of the hand in a stationary position. One or more vernierly adjustable, bent, pivotable bars 30 are mounted above the planar portion 14 of the bar support plate 12. Two such bars are depicted in FIG. 1. The pivotable bars 30 each have a finger support pad 36 at the outer end 15 thereof for applying pressure to a proximal phalanx of a MP joint, and a finely threaded adjustment screw 50 at the inner end 17. The adjustment screw is used to jack the inner end 17 of the pivotable bar 30 away from the support plate 12 and thereby increase the flexion of the joint, as is explained below in further detail.

As shown in FIG. 1, the support plate 12 is mounted on a hand by clamping it to the hand using a pair of clamps 18. Alternatively, the support plate 12 can be mounted to the hand in another suitable manner, such as by permanently attaching it to a separate hand splint. In contrast, if the device 10 is to be used to straighten a MP joint, the support plate 12 is mounted to the palm of the hand.

Figure 3:
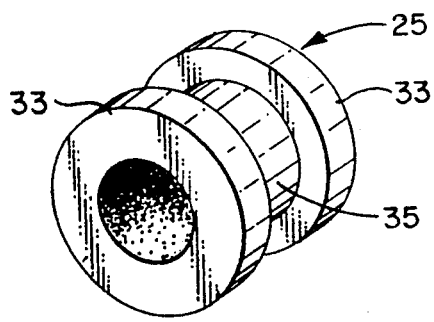
FIG. 3 shows a rubber bushing which is used to mount a bar support rod on the splint.

The support plate 12 has a pair of upstanding mounting flanges 20,22 extending perpendicularly upward from opposite longitudinal ends of the planar portion 14 of the support plate 12 for supporting an elongated, narrow, bar support rod 24 therebetween. The bar support rod 24 serves as a pivot axis for one or more of the pivotable bars 30. The bar support rod 24 preferably is spaced from the planar portion 14 of the support plate 12 by about one-quarter to one-third of an inch to facilitate pivoting of the pivotable bars 30 relative to the planar portion 14 of the support plate 12. Furthermore, the bar support rod 24 is in a plane which is generally parallel to the planar portion 14 of the support plate 12. Preferably, the bar support rod 24 is removably mounted to the upstanding mounting flanges 20,22 by a pair of barbell-shaped rubber bushings 25, shown in detail in FIG. 3. The bushings 25 each have a pair of hollow cylindrical, parallel heads 33 connected by a tubular portion 35. The heads 33 bear against opposite sides of the flanges 20,22. Each tubular portion 35 extends through a bore 27 in one of the flanges 20,22. The inner side of the tubular portion is knurled or otherwise textured in a manner that will help to hold the bar support rod in place therein. The bushings 25 can be manually removed from the apertures in the flanges 20,22 in order to add or remove one or more bars 30.

The support plate 12 can be made from a malleable material such as steel to allow for slight curving of the planar portion 14 to fit across the user's hand. The upstanding mounting flanges 20,22 must be sufficiently rigid, and must be connected with sufficient rigidity to the planar portion 14 in order to hold the bar support rod 24 in a stationary position relative to the planar portion 14. Preferably, the planar portion 14 and upstanding mounting flanges 20,22 are formed from a single metal sheet. The bar support rod 24 preferably is made of steel for convenience and economy, but can be made of any other material having sufficient support strength.

Each of the pivotable bars 30 generally has the same configuration. For purposes of discussion, references to the structure of a single pivotable bar 30 are intended to be applicable to each pivotable bar 30.

The pivotable bar 30 has a length of about 2-3 inches and a width and thickness of less than about ¼ inch each. The bar 30 is mounted on the bar support rod 24 between the upstanding mounting flanges 20,22 in a manner such that it can slide sideways along the bar support rod 24 when pushed with a reasonable force. In this manner, the bar 30 can be positioned directly above a metacarpal and corresponding proximal phalanx which form the MP joint of a particular finger. The bar support rod 24 is received in a transverse bore 28 through the pivotable bar 30. The bore 28 extends through the pivotable bar 30 in a direction perpendicular to its longitudinal axis, in order that the bar support rod 24 is normal to the pivotable bar 30 when the bar 30 is in a mounted position. A tubular bushing 29 made of rubber, plastic or another suitable material preferably is disposed in the bore 28 between the bar support rod 24 and the bar 30 to keep the bar 30 from sliding freely along the bar support rod 24, and to provide for an appropriate amount of friction when the bar 3 is pivoted.

The pivotable bar 30 preferably is bent manually inward toward the hand to form a bend 31 which corresponds generally to the angle between the metacarpal and proximal phalanx of the MP joint. The bend 31 defines an inner mounting leg 32, and an outer finger support leg 34. The transverse bore 28 is located on the mounting leg 32. The bend 31 provides the joint flexion device 10 with a streamlined appearance along the MP joint and minimizes the hindrance to the user. The bend 31 in the pivotable bar 30 preferably is made at a location between about two thirds and three-quarters of the length from one end of the pivotable bar 30 to the other in order to provide that the bar is not unnecessarily long. Preferably, the bend 31 is located near the transverse bore 28. The mounting leg 32 usually, although not necessarily, is shorter than the finger support leg 34. Generally, the angle of the bend 31 is between 180° and 90°, and usually is between 170° and 100°. Alternatively, the bar can be curved instead of being bent at an angle. When the pivotable bar 30 is mounted on the bar support rod 24, the bar support rod 24 is normal to the direction in which the pivotable bar 30 is bent or curved.

The pivotable bar 30 preferably is made of a malleable metal such as steel to allow for bending to fit the specific requirements of a patient while providing the necessary strength while in use. Alternatively, the bar can be made of aluminum or another alloy that is strong enough to hold the threads of screw 50. In the preferred embodiment of the invention, the bar remains substantially rigid during use.

Figure 4:
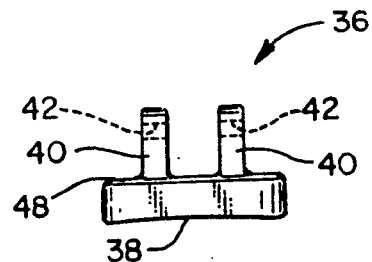
FIG. 4 shows an end view of a finger support pad which is used according to a preferred embodiment of the invention.

As shown in FIG. 1, the finger support pad 36 is adjustably mounted to the finger support leg 34 of the pivotable bar 30. The back of the finger support pad 36 has a support frame 48 which faces an inner side 37 of the pivotable bar 30, i.e. the side that forms an inside angle at the bend 31. As shown in FIGS. 1 and 4, the finger support pad 36 includes a support surface 38 which is suitably contoured for contacting the dorsal side of the finger along the proximal phalanx. Opposite to the support surface 38, the finger support pad 36 has a pair of outwardly extending, parallel flanges 40 between which the pivotable bar 30 is received. The flanges 40 have transverse bores 42 which are to be aligned on opposite sides of any one of several parallel, longitudinally spaced bores 44 in the outer leg 34 of the pivotable bar 30. The transverse bores 44 are parallel to the transverse bore 28 which receives the bar support rod 24. A fixation pin 46 is received in the bores 42 and 44 to fasten the phalanx support pad 36 to the pivotable bar 30. Preferably, the pin 46 has an interference fit in the flange bores 42 and is rotatable within bore 44. The pin can be removed by the physician or patient using a sharp instrument such as an ice pick in order to adjust the location of the support pad 36 along the bar 30. The choice of the particular transverse bore 44 around which the finger support pad is mounted will depend upon the size of the finger upon which the pivotable bar 30 is mounted. As mentioned above, the finger support pad 36 of the flexion device 10 should be positioned to contact the finger along the dorsal side of the proximal phalanx. On the other hand, if straightening of a MP joint is required, the phalanx support pad 36 should contact the anterior side of a finger along the proximal phalanx.

The curved support surface 38 of the phalanx support pad 36 preferably is made of pot or mold metal, and alternatively can be made of any relatively durable material which will be comfortable to the user and will not slide along the finger in a lengthwise direction as the pivotable bar 30 is vernierly adjusted. The flanges 40 are conveniently made of stainless steel, but can be made of any suitable material, and are attached to the slightly curved support surface 38 by the stainless steel support frame 48.

A finely threaded adjustment screw 50 having a large diameter knurled head 51 to allow for convenient tightening by hand, a threaded shaft 53, and a tip 54 is received in a threaded bore 52 on the mounting leg 32 of the pivotable bar 30. The threaded bore 52 is perpendicular to both the bore 28, which receives the bar support rod 24, and the longitudinal axis of the mounting leg 32. When the joint flexion device 10 is properly mounted on a hand, the tip 54 of the adjustment screw 50 bears against the planar portion 14 of the support plate 12. The adjustment screw is initially positioned in the threaded bore 52 in order that a lower end portion 55 of the shaft 53 is visible below the threaded bore 52 and an upper end portion 56 of the shaft 53 is visible above the threaded bore 52. Preferably, the upper end portion 56 initially has a length of about one-eighth of an inch or more. This arrangement permits the adjustment screw 50 to subsequently be vernierly rotated in a clockwise direction in order to bring the head 51 closer to the pivotable bar 30, and to move the outer tip 54 further from the pivotable bar 30, thereby further pivoting the pivotable bar 30 relative to the planar portion 14 of the support plate 12. The adjustment screw 50 can, if necessary, be rotated in a counterclockwise direction. As mentioned above, proper positioning of the pivotable bar 30 may require bending of the bar in order that it conforms with the angle of the MP joint.

As the angle between the outer leg 34 of the pivotable bar 30 and the support surface 14 is gradually increased or reduced by adjusting the adjustable screw 50, the angle formed by (1) the tip 54 of the screw 50, (2) the pivot axis of the pivotable bar 30, defined by the bar support rod 24, and (3) the center of the curved support surface 38 (with the pivot axis (2) forming the vertex of the angle), also is correspondingly increased or reduced. Furthermore, as this occurs, the distance between the tip 54 of the screw and the center of the support surface 38 is increased or decreased. As a result of the gradual reduction in the angle between the outer leg 34 and the support surface 14, the flexion of the MP joint is gradually increased.

As shown in FIG. 1, the bar support rod 24 can support several pivotable bars 30, and the bars 30 can be mounted along different fingers. When the bar support rod 24 is mounted to the support plate 12 in a removable fashion, the exact number of pivotable bars 30 required for a particular patient can be incorporated into the joint flexion device 10.

One of the important advantages of the vernierly adjustable bar of the invention is that after a physician mounts the device on a patient's hand, the patient can manually rotate the screw 50 himself in order to gradually increase the flexion of one or more MP joints. Furthermore, the flexion of each joint can be adjusted to a different angle or at a different rate.

Figure 2:
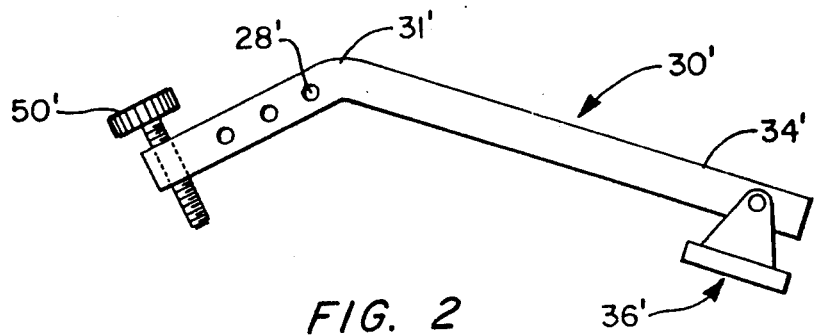
FIG. 2 shows a side view of the bar according to a second embodiment of the invention, in which the location of the pivot axis on the bar can be adjusted.

A second embodiment of the pivotable bar is shown in FIG. 2 and is designated as 30'. In this embodiment, a support pad 36' is nonadjustably mounted to an outer leg 34' of the pivotable bar 30'. Between the support pad 36' and a vernierly adjustable screw 50' at the opposite end of the bar 30' are three longitudinally spaced transverse bores 28' for alternatively receiving a bar support rod. The location of a bend 31' in this embodiment preferably is determined after a decision is reached as to which bore 28' will receive the bar support rod 28'. Generally, it is preferable to bend the pivotable bar 30' at a distance of about one quarter to one half an inch from the bore 28' which is to receive the bar support rod 24.

In another variation of the invention (not shown), the support pad is removably and rotatably connected to an elongated bar using a threaded mounting portion which is threadably received in vertical bore on the finger support leg of a pivotable bar. The threaded mounting portion has a knurled head which can be rotated to vernierly adjust the distance between the support surface of the support pad and the bar. The threaded mounting portion can be rotated without rotating the support pad. This configuration allows for vernier adjustment of the distance of the support pad from the pivotable bar without causing rotation of the support pad concurrently with the threaded mounting portion. Furthermore, in this embodiment, the bar can be stationary, rather than pivotable.

As will be apparent to persons skilled in the art, various modifications and adaptations of the structure above described will become readily apparent without departure from the spirit and scope of the invention, the scope of which is defined in the appended claims.

I claim:

1. A splint for flexing a metacarpophalangeal joint of a hand, comprising:
   bar support means to be mounted on the dorsal side of a hand in a stationary position relative to a metacarpal,
   a first bar pivotally connected to the bar support means, the first bar having longitudinally spaced ends and a pivot axis therebetween,
   a finger support pad formed on one end of the first bar for engaging a dorsal side of a first finger along a proximal phalanx which is connected to the metacarpal, and
   adjustment means formed on the other end of the first bar for vernierly adjusting the pivotal angle of the first bar relative to the support means when the support pad engages the first finger, the first bar remaining substantially rigid during adjustment.

2. A splint according to claim 1, wherein the adjustment means includes a threaded adjustment screw which can be threadably connected to the first bar.

3. A splint according to claim 2, wherein the threaded adjustment screw has a tip which bears against the bar support means during use of the splint.

4. A splint according to claim 3, wherein the threaded adjustment screw has a manually rotatable head.

5. A splint according to claim 1, wherein the bar support means includes a support plate, a pivot axis for the first bar comprising a transverse rod spaced from the support plate, and means for holding the rod in a stationary position relative to the support plate.

6. A splint according to claim 1, wherein the first bar is bent at an angle which is similar to the angle between the metacarpal and proximal phalanx.

7. A splint according to claim 6, wherein th first bar is configured to be bent to conform to the angle between the metacarpal and proximal phalanx prior to being connected to the support means.

8. A splint according to claim 1, further including means for adjusting the longitudinal position of the finger support pad on the first bar.

9. A splint according to claim i, further comprising a second bar having a finger support pad formed thereon for engaging the dorsal side of a second finger, the second bar having generally the same configuration as the first bar.

10. A splint according to claim 9, further comprising a third bar having a finger support pad formed thereon for engaging the dorsal side of a third finger, the third bar having generally the same configuration as the second bar.

11. A splint according to claim 10, further comprising a fourth bar having a finger support pad formed thereon for engaging the dorsal side of a fourth finger, the fourth bar having generally the same configuration as the third bar.

12. A splint according to claim 5, wherein the first bar is slidably mounted to the transverse rod.

13. A splint for flexing a joint connecting a proximal bone and a distal bond of a hand or foot, comprising:
bar support means to be mounted on a dorsal side of the hand or foot in a generally stationary position relative to one of the proximal bone and distal bond, the bar support means including a support plate, a transverse rod spaced from the support plate, and means for holding the rod in a stationary position relative to the support plate,
a first bar pivotally connected to the transverse rod, the first bar having longitudinally spaced ends and a pivot axis therebetween,
a support pad formed on one end of the first bar for engaging a dorsal side of the hand or foot along the other of the proximal bone and distal bone, and
adjustment means formed on the other end of the first bar for verinerly adjusting the pivotal angle of the first bar relative to the support plate when the support pad engages the hand or foot.

14. A splint according to claim 13, wherein the first bar is bent at an angle which generally corresponds to the angle between the proximal bone and distal bone.

15. A splint according to claim 14, wherein the first bar is configured to be bent to conform to the angle between the proximal bone and distal bone prior to being connected to the support means.

16. A splint according to claim 13, wherein the location of the support pad on the first bar is adjustable.

17. A splint according to claim 13, wherein the adjustment means includes a threaded adjustment screw which can be threadably connected to the first bar.

18. A splint according to claim 17, wherein the adjustment screw has a tip which bears against the support plate 19. A splint according to claim 18, wherein the adjustment screw has a manually rotatable head.

20. A splint according to claim 13, further comprising a second bar having a support pad formed thereon, the first and second bars being generally parallel.

21. A splint for flexing or straightening a joint connecting a proximal bone and a distal bone of a hand or foot, comprising:
bar support means to be mounted on the hand or foot in a generally stationary position relative to one of the proximal bone and distal bone, the bar support means including a support plate, a transverse rod spaced from the support plate, and means for holding the rod in a stationary position relative to the support plate,
a first bar pivotally connected to the transverse rod, the first bar having longitudinally spaced ends,
a support pad formed on one end of the first bar for engaging the hand or foot along the other of the proximal bone and distal bone, the location of the support pad on the first bar being adjustable, and
adjustment means formed on the other end of the first bar for vernierly adjusting the pivotal angle of the first bar relative to the support plate when the support pad engages the hand or foot.

* * * * *